United States Patent [19]
Lee et al.

[11] Patent Number: 6,109,917
[45] Date of Patent: Aug. 29, 2000

[54] SYSTEM FOR ESTABLISHING A REFERENCE PLANE FOR DENTAL CASTS

[75] Inventors: Robert L. Lee, deceased, late of Grand Terrace, by Arlene M. Lee, legal representative; Thomas E. Lee, Yucaipa, both of Calif.

[73] Assignee: Arlene M. Lee, Grand Terrace, Calif.

[21] Appl. No.: 09/023,970

[22] Filed: Feb. 13, 1998

[51] Int. Cl.[7] .................................................. A61C 19/04
[52] U.S. Cl. ................................................. 433/73; 433/68
[58] Field of Search ................................ 433/56, 57, 68, 433/73

[56] References Cited

U.S. PATENT DOCUMENTS

| | | | |
|---|---|---|---|
| 1,052,806 | 2/1913 | Evans . | |
| 2,235,524 | 3/1941 | Lentz . | |
| 3,084,438 | 4/1963 | Goodfriend | 433/73 |
| 3,224,096 | 12/1965 | Stuart . | |
| 4,084,319 | 4/1978 | Dragan | 433/73 |
| 4,537,574 | 8/1985 | Clark | 433/73 |
| 4,616,998 | 10/1986 | Wong | 433/73 |
| 4,695,252 | 9/1987 | Edwardson | 433/73 |
| 4,892,480 | 1/1990 | Levandoski | 433/73 |
| 4,909,737 | 3/1990 | Lee | 433/73 |
| 5,176,515 | 1/1993 | Andrews | 433/68 |
| 5,632,619 | 5/1997 | Polz | 433/68 |
| 5,738,517 | 4/1998 | Keller | 433/73 |

OTHER PUBLICATIONS

Pamphlet by Panadent Corp. entitled Bio–Esthetic™ Frontal Plane Level Gauge, copyright 1996, 3 pages.

*Primary Examiner*—Ralph A. Lewis
*Attorney, Agent, or Firm*—Knobbe, Martens, Olson & Bear LLP

[57] ABSTRACT

Dental apparatus which can determine a patient-specific reference plane so that the patient's teeth can be aesthetically oriented to an aesthetic axis-horizontal reference plane. The apparatus includes a face bow, an adjustable nasion relator assembly, a level gauge and a bite fork. The nasion relator assembly, along with the level gauge, enables the face bow to be moved to a level orientation.

15 Claims, 7 Drawing Sheets

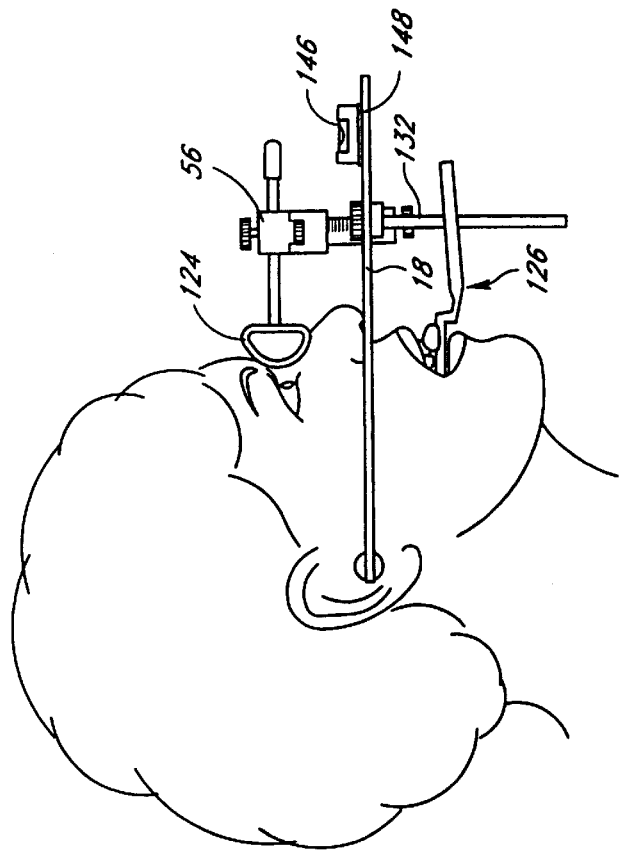
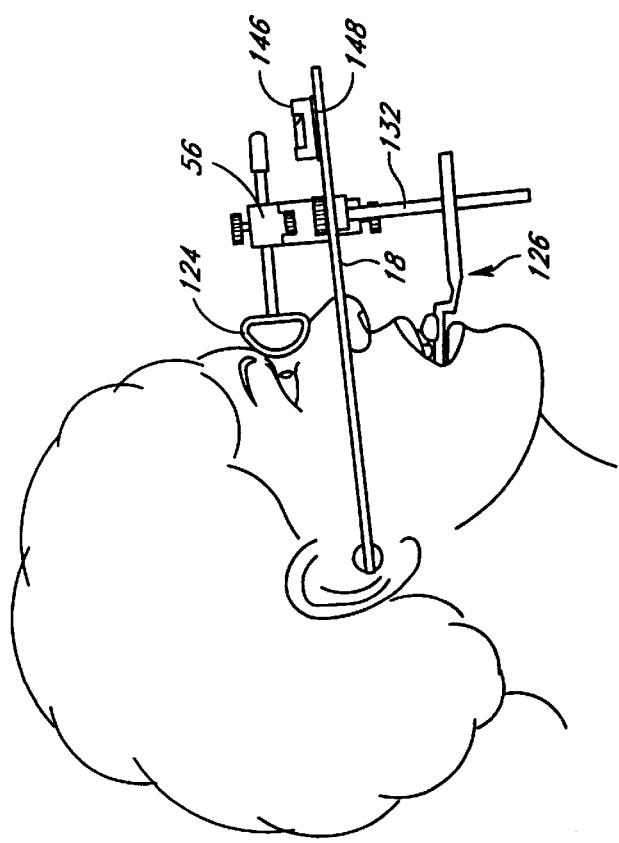

SYSTEM FOR ESTABLISHING A REFERENCE PLANE FOR DENTAL CASTS

BACKGROUND OF THE INVENTION

1. Field of the Invention

The present invention relates to dental apparatus and methods and more specifically to a system for orienting dental restorations to desired aesthetic reference plane(s).

2. Description of the Related Art

Dental restorations can usually be made functionally adequately in three planes of space (horizontal, vertical, frontal). However, too often dental restorations are made without sufficient attention to the aesthetic orientation of the patient's teeth. When in a proper erect standing or sitting position, the patient's maxillary anterior incisal-canine teeth line should ideally be with the horizon (horizontal reference plane) at a right angle to the patents mid-sagittal (vertical reference plane) when viewed from the patients front (frontal plane). The incisors midline should be vertical in the frontal plane (not angled). The angulations of the anterior teeth when viewed from the side of the patient (sagittal plane) is also important in diagnosing lip support for aesthetically pleasing smiles and proper facial profile. When aesthetically aligned, if the patient's head tilts from side to side, the incisal-canine teeth line will tilt with the head. To an observer, this slant of the teeth appears normal because the observer knows that when the head returns to the proper erect posture, the teeth will be horizontal again.

All three planes (horizontal, vertical, and frontal) are of aesthetic concern when diagnosing and providing dental care involving the orientation of teeth or gums, such as, restorative dentistry, prosthodontics, orthodontics, maxillafacial surgery, periodontics, gingivoplasty and other similar procedures.

There are many reasons why a dental patient may not naturally have the ideal aesthetic reference plane. Oftentimes, the teeth or skeletal bones are not properly or symmetrically formed in either the horizontal, vertical or frontal plane. Also, incorrect head posture disorients the teeth line. That is, some people have a chronic head tilt and seldom hold their head perfectly erect due to a number of causes such as occlusion, neuro-muscular, injuries, uneven leg lengths, compensatory scoliosis or osteoporosis. Further, a patient may have an atypical or unsymmetrical lip(s), lip line(s) or laughing line(s). This can also be due a number of causes such as ptosis (drooping) of the lips on one side of a patient's smile from a neurological problem, injury, tumor or a psychological compensatory mechanism.

Traditionally, when a patient underwent dental care involving the orientation of teeth, a double-bite tray impression of the anterior teeth segment was taken and sent to a dental laboratory. The laboratory technician would then make a dental cast and mount this cast in an articulator from which he could, for example, make and inspect false teeth for the patient. When mounting the dental cast in an articulator, the technician had no information regarding the spacial positional relationship between the patient's teeth and head, and thus, no information about a proper aesthetic reference plane which would align the patient's teeth in the articulator. Without this information, the technician would routinely make the anterior teeth line parallel to the articulator frame or the table-top. This alignment would be aesthetically proper only if the patient had a natural aesthetic reference plane, which is rare. The result of not incorporating the patient's aesthetic reference plane when the patient's dental cast is mounted on an articulator is a slanted anterior incisal-canine line, slanted gingival line, or both. Moreover, when the anterior incisal-canine line is made slanted, the maxillary mid-line (mid-sagittal) is also slanted, which is one of the most aesthetically serious errors.

As aesthetics became an increasing concern in the dental field, dental care providers tend to make the incisal-canine teeth line parallel to the interpupillary eye line when the patient is looking straight ahead. With this quasi standard, if one eye of a patient was higher than the other, which often occurs, the incisal-canine line was made slanted in relation to the horizon when the patient's head is erect. Face bows and articulators were then used to aesthetically measure and align a patient's teeth so that the incisal-canine plane was parallel to the interpupillary line as a chairside procedure in the provisionals, which were then given back to the lab for correction.

Early face bows used the "Frankfort-horizontal" plane of reference, which ran from the porion (top of the auditory meatus) to the orbitale (lower border of the orbit). U.S. Pat. No. 1,052,806 discusses an early face bow which used this reference plane. When a method for locating the hinge axis was later discovered, the two posterior points of the reference plane was moved from the porion down to the transverse hinge axis of the mandible, which is usually several millimeters below the porion. However, the anterior reference point was kept at the same orbital point or level, thus creating the "axis-orbital" plane of reference. The dental industry has standardized the average axis-orbital reference plane at 22 mm below the nasion, according to research studies.

There are many aesthetic problems related to the use of the axis-orbital reference plane. A brief illustration of three such problems is provided. First, when a standardized nonadjustable face bow is properly positioned on a patient, the face bow is usually slanted upward, because the orbital reference point is at the standard location of 22 mm below the nasion. This slanted face bow, in turn, slants a bite fork vertical attachment post forward in the sagittal plane. That is, the bite fork is angled. However, when a dental cast is mounted on the articulator, the attachment post is placed in a perfectly vertical position in the sagittal plane, and the face bow is perfectly parallel to the upper frame of the articulator in the horizontal plane. This difference in the bite fork angle changes the orientation of the maxillary cast in relationship to the horizontal reference plane. This error steepens the plane of occlusion in relationship to the upper frame of the articulator and similarly prevents a patient's teeth plane from being aesthetically aligned. Second, dental casts are mounted lower in an articulator than where a patient's teeth are physically located in relationship to the patient's head. This difference gives an illusion of a retrognathic mandible, or lingually inclined (tipped in) incisors since the casts have been rotated down and back around the axis, and prevents a patient's teeth plane from being aesthetically aligned. Third, as previously discussed, a patient's head, ears and teeth are rarely perfectly parallel. When the patient's head is erect and the ears are not even, the face bow is slanted and, in turn, slants the bite fork vertical post in the frontal plane. This error slants the teeth on the articulator and similarly prevents the patient's teeth plane from being aesthetically aligned.

In addition to the above-identified shortcomings of the axis-orbital reference plane, there is growing support that an "axis-horizontal" reference plane is the better aesthetic reference plane. When this aesthetic reference plane is obtained, the incisal-canine line will be made parallel to the horizon when the patient's head is perfectly erect, regardless of the eyes or any other facial feature. This view is based on, among other things, that the human eye is very keen to perceive objects in spacial relationships to horizontal and vertical and the degree of deviation from these reference positions. For example, when someone sees a picture on a wall that is tilted, there is a natural urge to straighten the picture. Moreover, most authorities agree that the most pleasing smile line is when the labial and buccal occlusal edges of the maxillary teeth follow the curvature of the lower lip and radiate symmetrically back to the comissures of the lips. The anterior teeth should also be labial inclined (tilted out) for lip support. Since many people's head and facial features are unsymmetrical, the better method of establishing an aesthetic base line would be to have the aesthetic reference plane in the axis horizontal plane when the patient is in the proper erect position.

There is thus a need for a method and apparatus which measures a patient-specific aesthetic reference plane. There is also a need to relate this information to an articulator so that the patient's dental cast mounted therein can be aesthetically aligned in the axis-horizontal reference plane.

SUMMARY OF THE INVENTION

In accordance with a method of the invention, a dental face bow is adjusted and connected to a dental bite fork to obtain a desired aesthetic orientation of the bite fork for mounting casts in a dental articulator. In a first step of the method, the bite fork is positioned in a patient's mouth in registration with the patient's teeth or gums, with a rod of the bite fork extending forwardly from the patient's mouth. The patient is directed to sit in an erect position. A face bow is mounted on the patient with an ear plug on each of two side sections of the face bow and is positioned in a respective one of the patient's ears. A nasion relator assembly is mounted on the face bow, with a nasion relator positioned on the patient's nasion. By adjusting the mounting between the nasion relator assembly and the face bow, a side section of the bow is placed in a substantially horizontal orientation in an anterior-posterior direction (sagittal plane). This may conveniently be accomplished by vertically adjusting the nasion relator assembly and observing a small bubble level gauge positioned on the face bow side section with the level gauge oriented in that anterior-posterior direction. Next, the face bow is tilted in the patient's ears to a substantially horizontal position in a side-to-side direction (frontal plane). Again, this may be done by observing a properly oriented level gauge in a side-to-side direction. With the face bow so oriented, level to the axis-horizontal plane of reference, the bite fork is fixed to the face bow. The bite fork registers orientation the teeth to that horizontal plane. This then orients the face bow to the patient in sagittal, frontal and horizontal planes.

Another aspect of the invention is the combination apparatus used in the above-described method. More specifically, the combination of the face bow, the adjustable nasion relator, bubble level gauge, the bite fork, and bite fork stem create a patentable combination. The connection between the face bow and the bite fork stem is typically a horizontally connecting rod and a vertical attachment post and suitable clamps. The bite fork and the attachment post can be separated from the face bow and mounted to a horizontal dental articulator frame, with the vertical attachment post connected to the frame. The bite fork is then in the desired orientation for receiving a dental cast, after which the cast is joined to the frame with plaster or other suitable means. The articulator can then be manipulated to simulate the patient's jaw movements.

Yet another aspect of the present invention is the adjustable nasion relator assembly. The nasion relator has a shaft having one end connected to and extending outwardly from the relator and the other end being connected to a housing. The nasion relator assembly also has an extension element configured to be connected to a face bow. The extension element is also connected to the nasion relator housing in a vertically adjustable manner so as to enable the face bow to be vertically adjusted relative to the nasion relator. In a preferred arrangement, an adjusting thumb screw is rotatably captured in a housing which is mounted in the nasion relator assembly and the screw shank is connected to the extension element. Thus, rotating the thumb screw, vertically moves the element.

BRIEF DESCRIPTION OF THE DRAWINGS

FIG. 5a is a side elevational view of the apparatus of FIG. 1 before it is adjusted in the sagittal plane;

FIG. 5b is a side elevational view of the apparatus of the FIG. 5a after it is adjusted in the sagittal plane;

DETAILED DESCRIPTION OF THE PREFERRED EMBODIMENT

Figure 1:
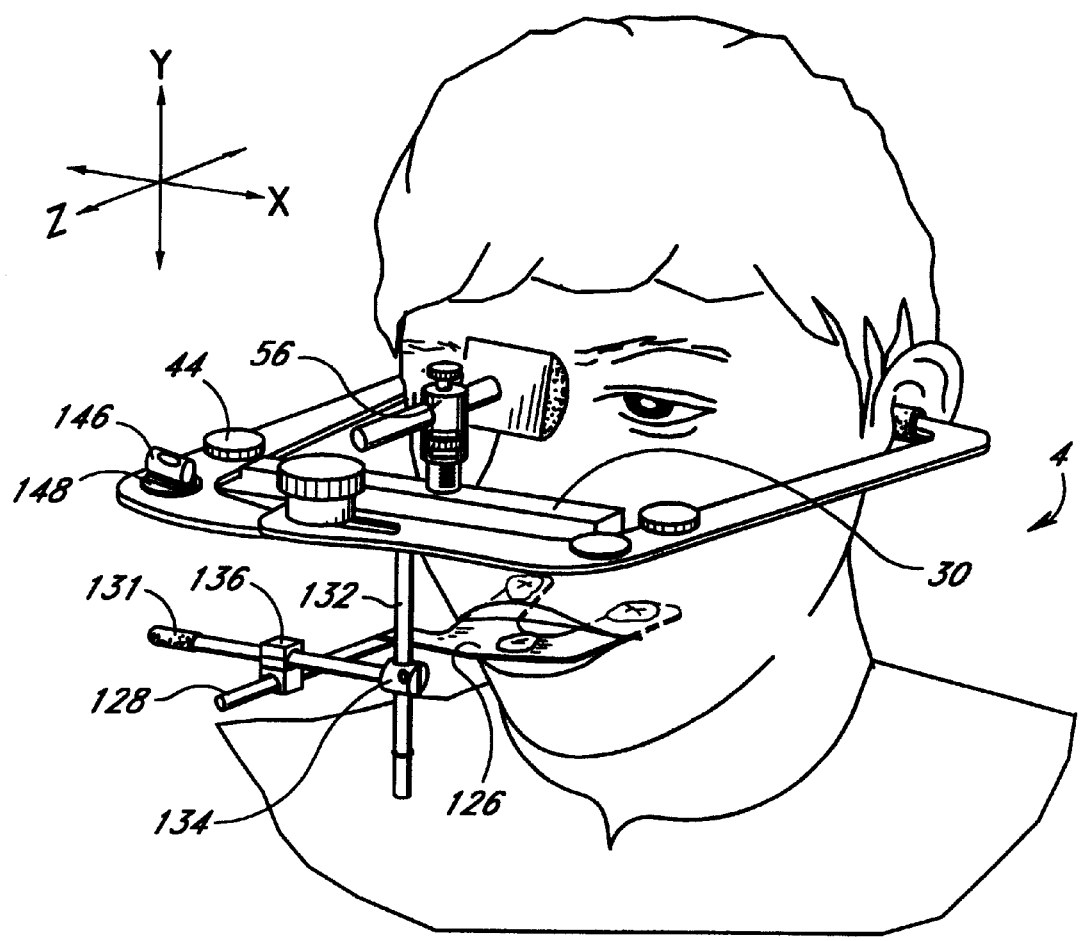
FIG. 1 is a perspective view of a apparatus attached to a patient to establish an aesthetic reference plane along an axis-horizontal plane.

The system for establishing an aesthetic reference plane is discussed in context of a face bow apparatus from which a dental cast of a patient's teeth can be mounted in an articulator. To assist in the description of the components of the face bow apparatus and system for establishing an aesthetic reference plane, the following coordinate terms are used. Referring to FIG. 1, an anterior-posterior Z—Z axis extends along the depth of a patient's body, from the rear of the patient to the front of the patient. A vertical Y—Y axis is perpendicular to the anterior-posterior Z—Z axis and extends generally along the vertical height of the patient's body. A horizontal X—X axis extends along the width of a patient's body from the left side of the body to the right side of the body. A horizontal plane is a plane parallel to the horizon and aligned in the horizontal X—X axis and anterior-posterior Z—Z axis. A vertical plane is parallel to a patient's mid-sagittal plane and aligned in the vertical Y—Y axis and anterior-posterior Z—Z axis. A frontal plane is parallel to the front of a patient's face and aligned in the horizontal X—X axis and vertical Y—Y axis.

Precise placement of a dental cast in an articulator is required to aesthetically align a patient's teeth. Referring to FIG. 1, a face bow 4 provides accurate positioning of teeth impressions made onto a bite fork 126 relative to an aesthetic reference plane. The bite fork 126 is fixed to the face bow 4 by a vertical post 132, a horizontal rod 131 and suitable clamps 134 and 136. A nasion relator assembly 56 is also fixed to the face bow 4. A bubble level gauge 146 mounted to the face bow 4 is used to determine when the face bow is level in the horizontal plane. When properly positioned, dental impressions of a patient's teeth will be aesthetically orientated to the axis-horizontal plane of reference. A dental cast of the patient's teeth can be made and placed in an articulator to the patient-specific axis-horizontal reference plane. Dental care can then be provided utilizing the aesthetic reference plane as a guide.

Components

Figure 2:
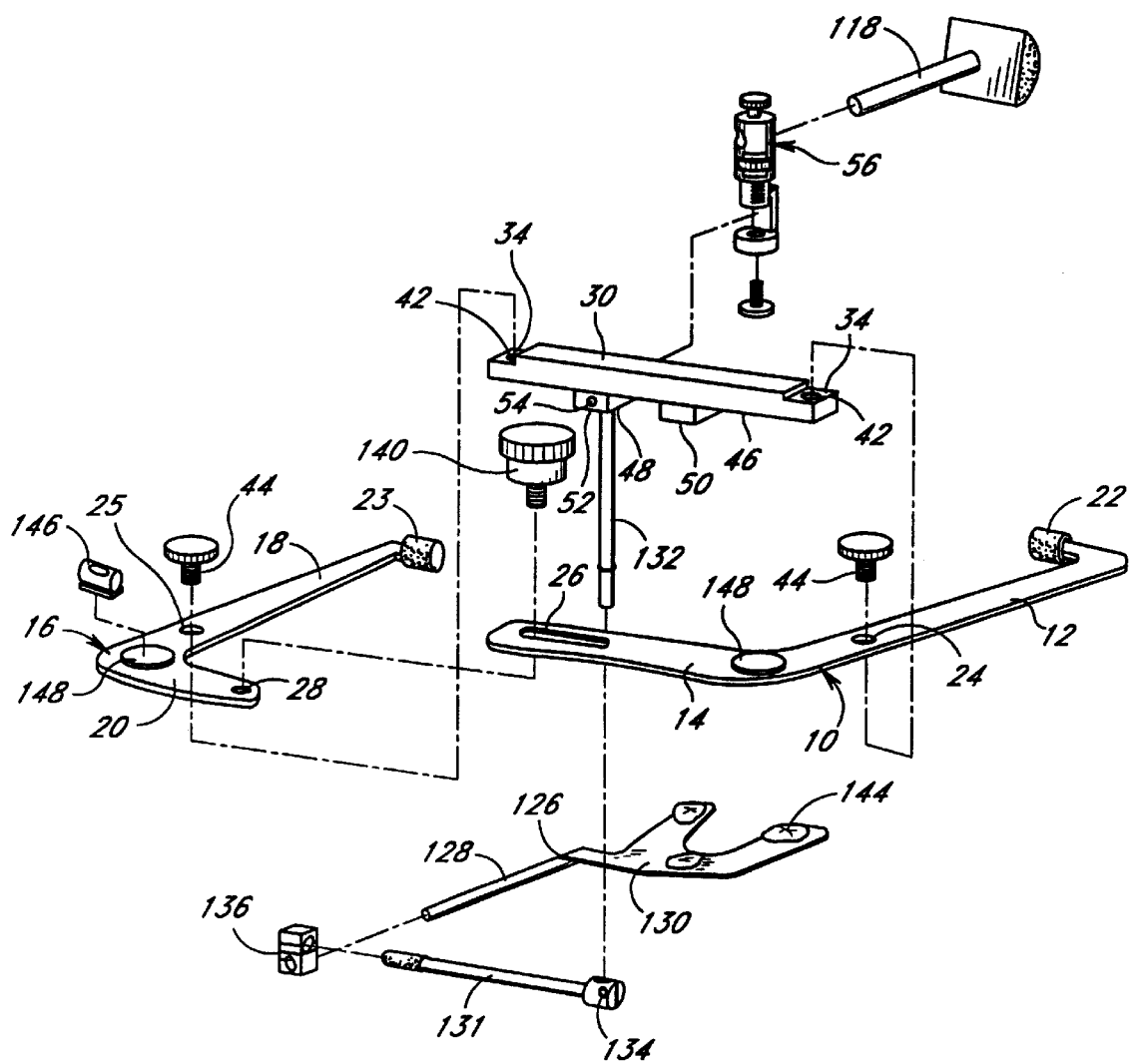
FIG. 2 is an exploded perspective view of the apparatus of FIG. 1.

Referring to FIG. 2, the face bow 4 has a generally L-shaped first extension arm 10 with a side section 12 and a front section 14. A second extension arm 16 of similar L-shaped design also has a side section 18 and a front section 20. Ear plugs 22, 23 are positioned on rear ends of the side sections 12, 18. Mounting holes 24, 25 are formed in the side sections 12, 18 slightly to the rear of the front sections 14, 20. A transversely extending slot 26 is formed in the front section 14 of the first extension arm 10 spaced from the side section 12. A threaded hole 28 is formed on the front section 20 of the second extension arm 16 spaced from the side section 18.

A cross bar 30 has recessed ends 34, with each having a threaded aperture 42. A bottom face 46 of the cross bar 30 has a pair of centrally located spaced lugs 48 and 50 formed thereon. The lug 48 has a socket 52 in its lower surface, and extending along the vertical Y—Y axis, capable of receiving the vertical attachment post 132. The lug 48 also has a hole 54 for receiving a set screw to secure the post 132 to the cross bar 30.

Figure 3:
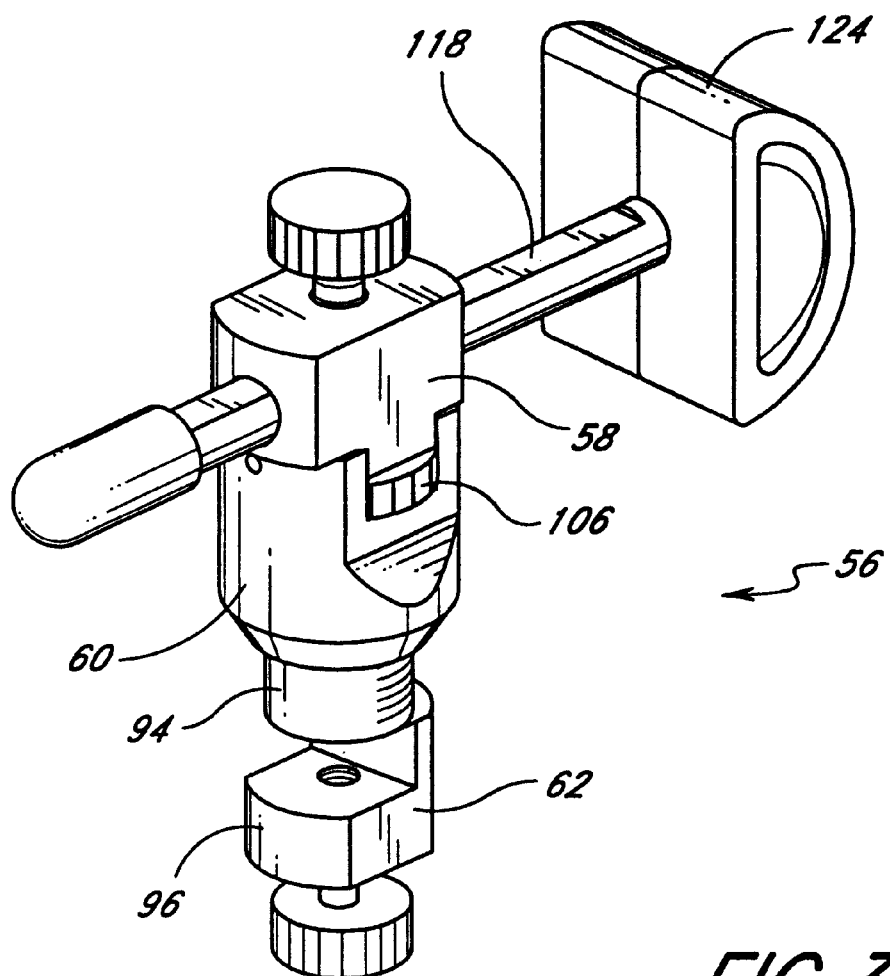
FIG. 3 is a detail perspective view of the nasion relator assembly of FIG. 1.
Figure 4:
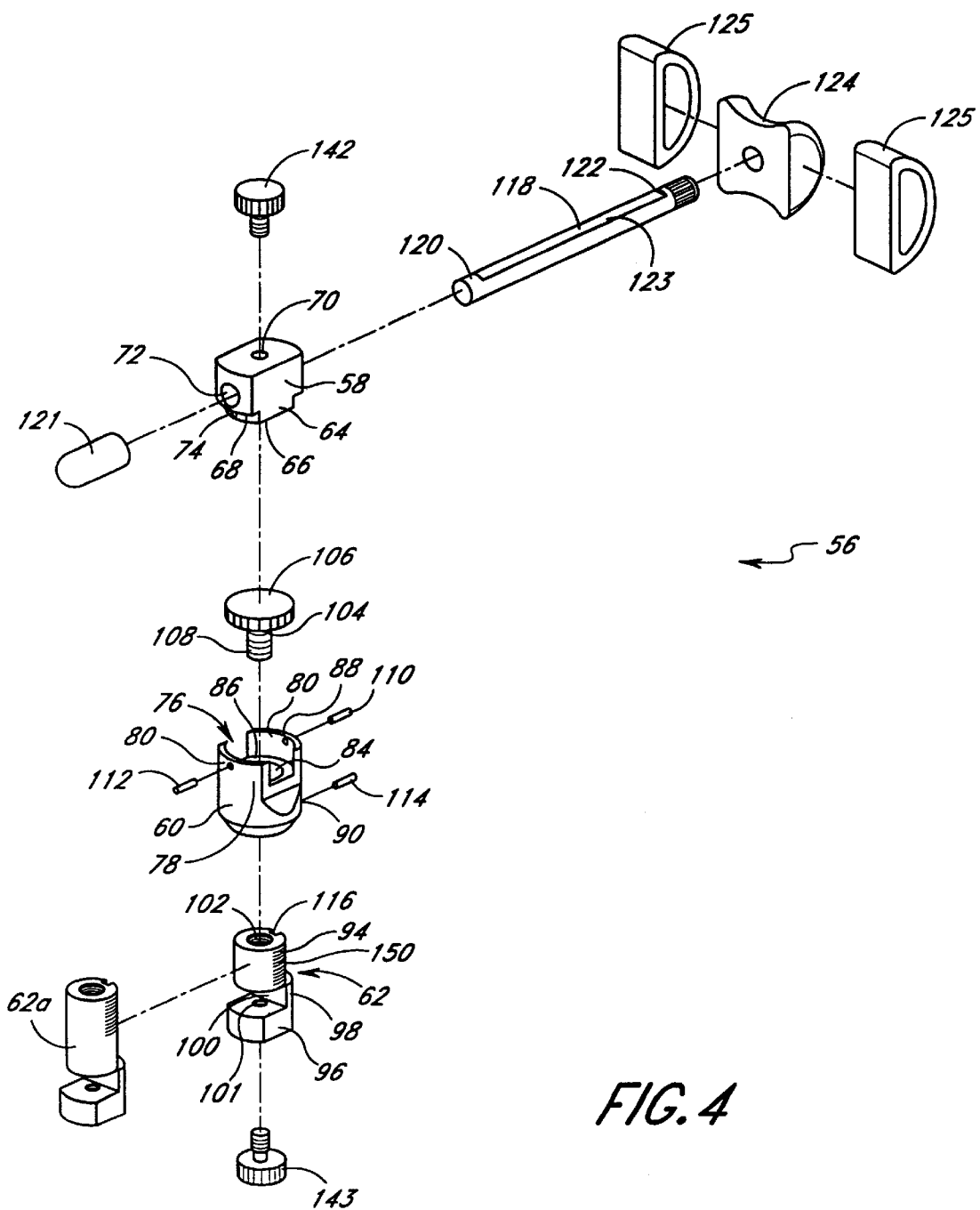
FIG. 4 is an exploded perspective view of the assembly of FIG. 3.

FIGS. 3 and 4 show a nasion relator assembly 56 having an upper housing section 58, a lower housing section 60 and an extension element 62. The upper housing section 58 preferably has curved front and rear sides, and flat, truncated sides. A lower portion 64 of the upper housing section 58 is preferably similarly configured, but the diameter of the curved faces is smaller than the diameter of the curved faces of the upper portion so that a lip 68 is formed on each end. A hole 72 extends parallel to the Z—Z axis through the upper housing section 58 for receiving a nasion relator shaft 118. A threaded bore 70 for receiving a thumb screw 142 extends parallel to the vertical Y—Y axis. A small opening 74 also extends along the Z—Z axis through the lower portion 64 of the upper housing section 58, parallel to and vertically below the hole 72.

The lower housing section 60 of the nasion relator assembly 56 is generally cylindrically shaped with a conical taper on its bottom end. A recess 76 is formed on a top portion 78 of the lower housing section 60, partially surrounded by diametrically spaced walls 80 which are cylindrical segments with an outside diameter as the lower portion of the lower housing section 60. The outer diameter of the walls 80 of the lower housing section is approximately the same as the outer diameter of the upper housing section 58. The inside diameter of the walls 80 of the lower housing section 60 is slightly larger than the outer diameter of the lower portion 64 of the upper housing section 58 so that such portion fits between the walls 80 and within the recess 76. A bore 84 extends in the vertical Y—Y axis through the lower housing section 60. The diameter of the bore 84 is smaller than the inside diameter of the walls 80 so that a ledge 86 is formed between the bore 84 and walls 80. A small opening 88 extends along the Z—Z axis through each of the walls 80 of the lower housing section 60. A small opening 90 extends along the Z—Z axis parallel to and below the opening 88 and opens into the bore 84.

The extension element 62 of the nasion relator assembly 56 has a cylindrical top portion 94 sized to be received into the vertical bore 84 in the lower housing section 60. A bottom portion 96 of the extension member 62 is configured similar to the upper housing section 58, having curved front and rear faces, and flat, truncated sides. The portions 94 and 96 are spaced to provide a gap 100 for receiving the face bow cross bar 30. A middle portion 98 of the extension member 62 joins the upper and lower portions. A threaded bore 102 extends in the vertical Y—Y axis through the upper portion 94 of extension member 62 to receive the shank 108 of the lead screw 104. A threaded bore 101 extends in the vertical Y—Y axis through the lower portion 96 of the extension member 62 to receive thumb screw 143 for attaching to the cross bar 30.

A lead screw 104 with a head 106 and a shank 108 is placed between the upper and lower housing sections 58, 60. The diameter of the head 106 is smaller than the inside diameter of the walls 80 of the lower housing section 60 but larger than the bore 84 of the lower housing section 60, so that the head 106 is loosely captured in the recess 76 of the lower housing section 60 and rests on the ledge 86. Because of the truncated sides of the lower housing section 60, edges of the screw head 106 protrude and can be easily manually rotated. The shank 108 of the lead screw 104 extends vertically through the bore 84 and threads into the bore 102 in the extension member 62. As seen from FIG. 3, the lower portion 64 of the upper housing section 58 fits within the recess 76 in the lower housing section 60 and the lips 68 of the upper housing section 58 rest atop the walls 80 of the lower housing section 60. A pair of small pins 110 and 112 inserted through the small openings 88 in the side walls 80 of the lower housing section 60 and into small openings 74 of the upper housing section 58 and hold the housing sections 60, 58 together.

A small pin 114 extends through the small opening 90 of lower housing section 60 and into groove 116, that extends parallel to the vertical Y—Y axis on the exterior of the cylindrical extension element 62. This pin 114 inhibits rotation of the extension element 62 when the lead screw 104 is rotated while allowing the extension element 62 to vertically move. If the extension element 62 does not provide a sufficient downward movement, the longer version 62a shown in FIG. 4 may be employed instead.

The terminal portion of the nasion relator shaft end 120 is preferably covered by a soft cap 121 for safety concerns and to prevent the stem from falling out. The other end 122 of the shaft 118 is fixed to a nasion relator 124 and is preferably covered by pads 125 for patient comfort.

FIG. 2 depicts a bite fork 126 having an elongated rod or stem 128 integrally formed with a mouthpiece 130. An adjustable horizontal mounting rod 131 has a double-toggle clamp 136 slidably positioned thereon for attaching to the bite fork stem 128. A single-toggle clamp 134 on the rod 131 adjusts and secures the rod to an attachment post 132, which in turn connects to the face bow cross bar 30 in the vertical Y—Y axis, discussed in greater detail below.

Assembly

The present system for establishing an aesthetic reference plane requires that the dental device detailed above be properly assembled prior to use. Assembly can be performed as directed below.

Referring to FIG. 2, position the first and second face bow extension arms 10, 16 so that the front section 14 of the first extension arm 10 lies atop and abuts the front section 20 of second extension arm 16, and the slot 26 on the first extension arm 10 aligns with the threaded hole 28 on the second extension arm 16. Pass the thumb screw 140 through the slot 26 and secure the thumb screw 140 to the threaded hole 28 with the arms in a desired position. Place the side sections 12, 18 of the extension arms 10, 16 on top of the recessed ends 34 of the cross bar 30 so that threaded apertures 42 align with the holes 24, 25 of extension arms 10, 16 and attach with the shoulder screws 44.

Referring to FIG. 4, as well as FIG. 2, attach the shaft 118 of the nasion relator assembly 56 to the upper housing section 58 of the nasion relator 56 by passing the shaft 118 through the hole 72. Secure it with a thumb screw 142 inserted through the threaded vertical bore 70 to engage the shaft 118. Attach the nasion relator assembly 56 to the cross bar 30 by orienting the gap 100 of the extension member 62 so that the middle portion 98 engages the cross bar 30 with the bottom portion 96 between the lugs 48, 50. Tighten a thumb screw 143 to secure the nasion relator assembly 56 to the cross bar 30.

Referring to FIG. 2, attach the post 132 to the cross bar 30 by placing the post end into the socket 52 formed in the cross bar lug 48. Secure the post 132 to the cross bar 30 with a set screw through the hole 54. The bite fork stem 128 should not be attached to the attachment post 132 at this point. Also, the single and double toggle clamps 134, 136 should be loose.

Operation

To obtain a proper aesthetic reference position, the patient should preferably sit perfectly erect on a backless chair or stool and look straight ahead at a wall or mirror while holding the head level. Sitting is preferred to standing because it is difficult for a patient to maintain a perfectly erect body position for an extended period of time while standing, and standing makes it more difficult for the dental care provider or patient to reach and adjust the face bow.

Take a conventional bite fork registration whereby a compound 144 is placed on the mouthpiece 130 of the bite fork 126, the bite fork 126 is properly positioned in the patient's mouth and the patient bites on the compound 144. Remove the bite fork 126 from the patient's mouth so the compound 144 can harden and the registration can be inspected. After inspecting the registration, return the bite fork 126 into the patient's mouth.

Secure the face bow 4 to the patient's ears by placing the ear plugs 22, 23 into the patient's ears, respectively. Adjust the face bow 4 with the thumb screw 140 so that the side sections 12, 18 of the face bow 4 gently, but firmly, grasp and are supported by the patient's ears. Position the nasion relator 124 against the patient's nasion by extending the elongated shaft 118 toward the patient's nasion. Adjust the position of nasion relator 124 so it gently, but firmly, engages and is supported by the patient's nasion. Tighten the thumb screw 142.

Because the patient will rarely have a natural aesthetic reference plane, the face bow 4 will usually not be perfectly aligned in the sagittal plane (usually due to the third point of reference) and the attachment post 132 will usually not be perfectly parallel to the vertical Y—Y axis. FIG. 5a shows the face bow 4 in such a configuration where the face bow 4 is upwardly angled and the attachment post 132 is outwardly angled from face bow 4.

Position bubble level gauge 146 on top of the face bow side section 18 or 12 with the level gauge length extending in the anterior-posterior direction so as to obtain a reading in that direction related to the sagittal plane. Preferably, the level gauge 146 is magnetically secured to a metal disc 148 on the face bow 4 by a magnet attached to level gauge 146.

Figure 6B:
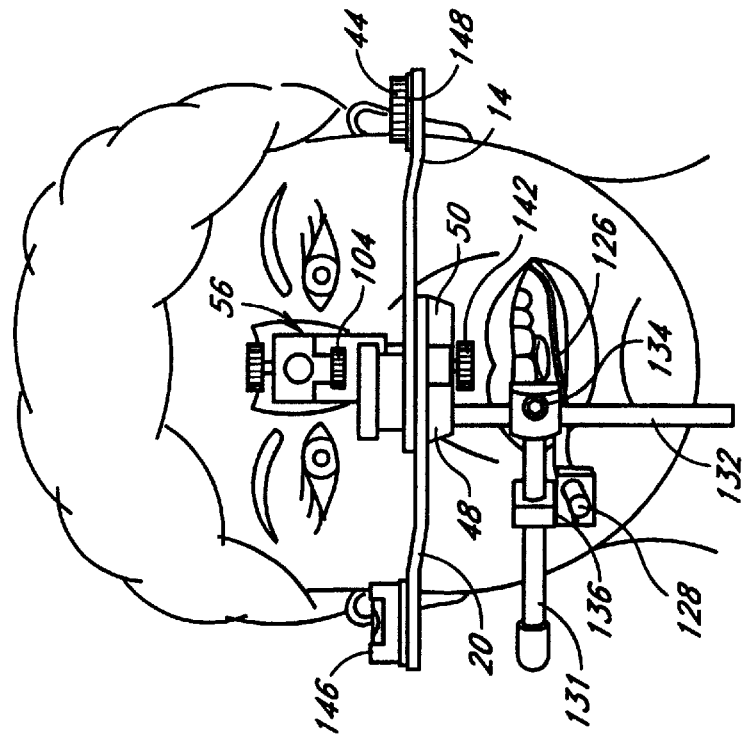
FIG. 6b is a front elevational view of the apparatus after the apparatus is adjusted in the frontal plane and oriented aesthetically to the patient in the frontal, horizontal and sagittal planes.
Figure 6A:
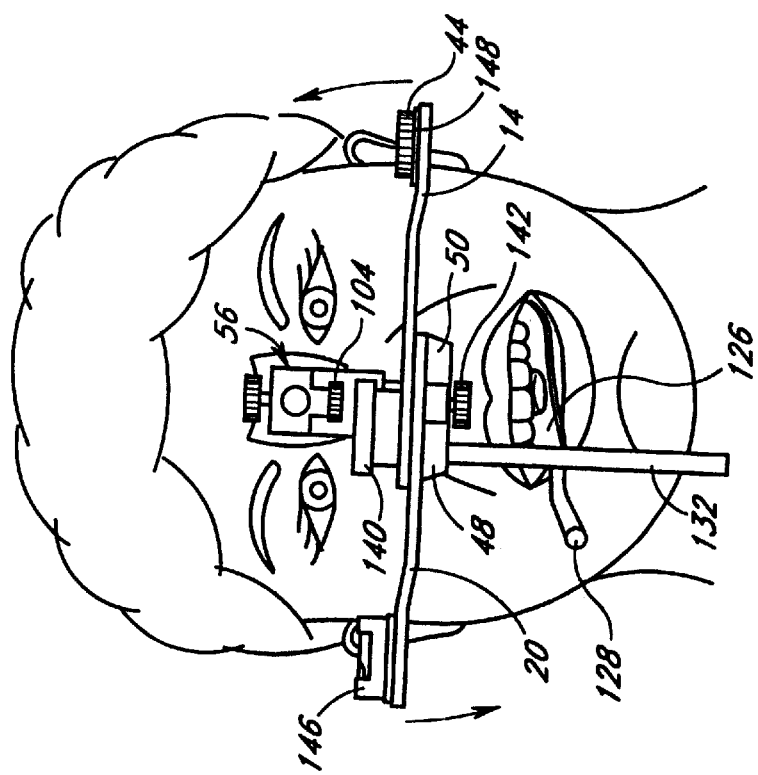
FIG. 6a is a front elevational view of the apparatus of FIG. 1 before the apparatus is adjusted in the frontal plane.

Turn the lead screw 106 on the adjustable nasion relator assembly until the level gauge 146 indicates that the side section 18 or 12 of the face bow is level in the anterior-posterior direction. Record a numerical setting 150 indicated on the extension member 62 of the nasion relator assembly 56. This is the distance, preferably in millimeters, of the anterior reference point as measured from the nasion which will align the patient's teeth in the sagittal plane. FIG. 5b shows the face bow 4 side sections parallel to the Z—Z axis and the attachment post 132 in a plane parallel to the Y—Y axis. That is, the post appears vertical from the side, viewed in relation to the sagittal plane, although, as will be seen from the frontal view in FIG. 6a, the post is not yet truly vertical. Similarly, although each face bow side section is level in the anterior-posterior direction, the face bow 4 will usually not be perfectly horizontal (usually due to one ear meatus being higher that the other). FIG. 6a shows the face bow 4 in such a configuration. To obtain a reading along the horizon, rotate the level gauge 146 to the side-to-side orientation, shown in FIG. 6a.

Insure the patient maintains a perfectly erect posture while looking straight ahead. To assist with this posture, a hand or book can be placed on the patient's head or other similar posture perfecting device can be used. Tilt the face bow 4 until the level gauge 146 indicates that the bow is level, parallel to the horizontal X—X axis. Either the patient, dental care provider or an assistant can perform this tilting operation. With the face bow so held, tighten the double toggle clamp 136 to secure the bite fork 126 to the connecting rod 131 in the plane of the Z—Z and X—X axes. Tighten the single toggle clamp 134 to secure the connecting rod 131 to the attachment post 132 in the vertical Y—Y axis. When tilting the front of the face bow into a horizontal position, one side section moves up and the other moves down. Since the face bow is relatively rigid, the portions contacting the patient's ears also move correspondingly. The ear tissue is sufficiently pliable to accommodate such movement.

Figure 7:
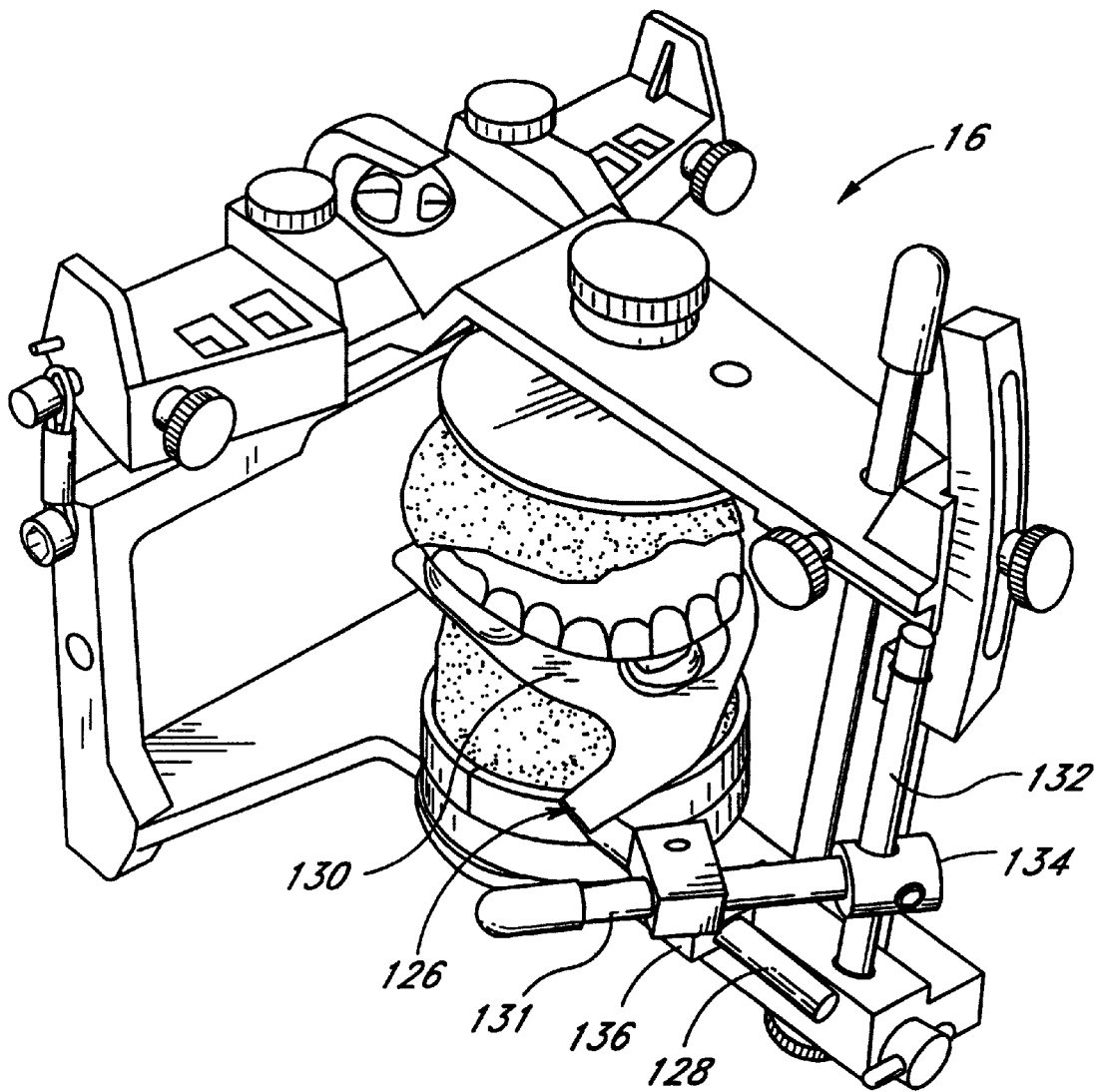
FIG. 7 is a perspective view of a dental cast in an axis-horizontal aesthetic reference plane mounted in an articulator.

By the above described method, a patient specific reference plane can be measured with a face bow and the patient's teeth can be aesthetically oriented in the sagittal, frontal and horizontal planes on an articulator. FIG. 7 shows the bite fork 126 placed into an articulator for mounting the patient's maxillary cast using plaster or other known procedure. When so mounted, the slant of the occlusal plane, titled midline and/or gingival line is obvious when viewed from the front or side. A diagnosis can be made for aesthetic correction of the patient's teeth using the frames of the articulator as an aesthetic reference guide. Thus, for example if frontal teeth restorations are to be made, the desired aesthetic changes can be recognized from viewing the patient's dental casts in the articulator. Such restorations can later be made in the articulator to achieve the desired effect.

The face bow 4, cross bar 30, bite fork 126, adjustable nasion relator 56 and level gauge 146 are constructed of suitable metals, plastic or other materials which are relatively stiff, strong and easily cleaned.

The embodiments illustrated and described above are provided merely as examples of the aesthetic reference plane to be used with the dental device in accordance with the present invention. Other changes and modifications can be made from the embodiments presented herein by those skilled in the art without departing from the spirit and scope of the invention as defined by the appended claims.

What is claimed is:

1. A method of adjusting and connecting a dental face bow to a dental bite fork to obtain a desired aesthetic orientation of the bite fork for mounting in a dental articulator, comprising the steps of:

positioning the bite fork in a patient's mouth in registration with the patient's teeth or gums, the bite fork including a rod extending outwardly from the patient's mouth;

directing the patient to sit in an erect aesthetic reference position;

mounting a face bow on the patient with an ear plug on each of two side sections of the face bow positioned in the meatus of a respective one of the patient's ears, said bow including a nasion relator assembly mounted thereon and said mounting step including positioning a nasion relator on the patient's nasion;

adjusting the mounting between the nasion relator assembly and the face bow so as to place a side section of the bow substantially level in an anterior-posterior direction beneath the patient's nasion;

tilting the face bow so that a front section joining the side sections of the face bow is substantially level in a side-to-side direction; and fixing the bite fork to the face bow while the face bow is substantially level, to thereby fix the bite fork in a desired orientation in relation to sagittal, frontal and horizontal planes for mounting in a dental articulator.

2. The method of claim 1, including removing the face bow from the patient and transferring the bite fork assembly to a dental articulator for mounting a patient's dental cast in the articulator.

3. The method of claim 1, wherein said adjusting step includes moving said face bow front section vertically.

4. The method of claim 3, wherein said nasion relator assembly includes a rod extending forwardly from the nasion relator, a housing mounted on said stem, and an extension member clamped to a face bow cross bar extending between said face bow side sections, and said adjusting step includes vertically moving said extension member.

5. The method of claim 4, wherein said nasion relator assembly includes an adjusting screw captured within said housing and having a shank threadably connected to said extension member, and said adjusting step includes rotating said adjusting screw to move the extension member vertically.

6. The method of claim 1, including separating the bite fork from the face bow and mounting the bite fork to a frame of a dental articulator with the frame being generally horizontally oriented.

7. The method of claim 6, including positioning a dental cast in registration with the bite fork and connecting the dental cast to a frame of the dental articulator.

8. The method of claim 1, wherein said adjusting step includes observing a bubble level gauge mounted on one of said side sections with the level gauge extending in said anterior-posterior direction, and stopping said adjusting when the bubble level gauge indicates that said side section is level; and said tilting step includes positioning a level gauge on said face bow front section with the level gauge extending in said side-to-side direction, and stopping said tilting when the level gauge indicates that said front section is level.

9. A dental apparatus including an adjustable nasion relator assembly comprising:

a nasion relator formed to be positioned on a nasion of a patient, the nasion relator including a housing having an upper section and a lower section having an interior cavity formed to capture a head of an adjusting screw with a portion of the head extending through a sidewall of the housing such that the head may be manually rotated from an exterior of the housing, and the housing further including a space in which a shank of the adjusting screw extends, a shaft having one end connected to and extending forwardly from said relator; and an extension element connected to the adjusting screw shank configured to be connected to a face bow, the extension element being connected to the housing in a vertically adjustable manner so as to enable the face bow to be vertically adjusted relative to the nasion relator.

10. The apparatus of claim 9, wherein said housing upper section includes a hole receiving said nasion relator shaft.

11. The apparatus of claim 9, wherein the assembly includes an adjustment screw having a head rotatably captured within the housing and having a shank which is connected to the extension element in a manner such that rotation of the screw will move the element vertically toward or away from the housing.

12. The apparatus of claim 9, wherein the extension element extends into a bore in the housing, and the extension element cooperates with the housing in a manner that permits the extension element to move axially with respect to the housing but restricts the extension element from rotating with respect to the housing.

13. The apparatus of claim 9, wherein the extension element includes numerical settings to measure the distance of an anterior reference point as measured from a nasion to align the patient's teeth in a sagittal plane.

14. The apparatus of claim 13, wherein the numerical settings are marked uniformly along the length of the extension element.

15. The apparatus of claim 13, wherein the numerical settings allow recording of the anterior reference point so that the particular alignment of the patient's teeth in the sagittal plane can be reproduced without reapplying the dental apparatus to the patient.

* * * * *